(12) United States Patent
Caravatti et al.

(10) Patent No.: US 7,625,894 B2
(45) Date of Patent: Dec. 1, 2009

(54) PYRROLO[2,3-D]PYRIMIDINES AS PROTEIN TYROSINE KINASE INHIBITORS

(75) Inventors: Giorgio Caravatti, Bottmingen (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/598,070

(22) PCT Filed: Feb. 17, 2005

(86) PCT No.: PCT/EP2005/001635

§ 371 (c)(1),
(2), (4) Date: Aug. 17, 2006

(87) PCT Pub. No.: WO2005/077951

PCT Pub. Date: Aug. 25, 2005

(65) Prior Publication Data

US 2007/0135460 A1    Jun. 14, 2007

(30) Foreign Application Priority Data

Feb. 18, 2004    (GB) ................... 0403606.7

(51) Int. Cl.
    C07D 487/04    (2006.01)
    C07D 413/12    (2006.01)
    A61K 31/5355   (2006.01)
    A61K 31/519    (2006.01)
    A61P 35/04     (2006.01)

(52) U.S. Cl. .................... 514/234.2; 544/280; 544/118; 514/265.1

(58) Field of Classification Search ............ 544/280, 544/118; 514/265.1, 252.16, 234.2
    See application file for complete search history.

(56) References Cited

U.S. PATENT DOCUMENTS 7,253,166 B2 * 8/2007 Ding et al. ............... 514/234.2

FOREIGN PATENT DOCUMENTS

| EP | 0 888 349 B1 | 1/1999 |
| WO | WO98/07726 A1 | 2/1998 |
| WO | WO99/65909 A1 | 12/1999 |
| WO | WO03/013541 A1 | 2/2003 |
| WO | WO2003/037897 A2 | 5/2003 |
| WO | WO2005/067546 A2 | 7/2005 |
| WO | WO2005/075460 A2 | 8/2005 |

OTHER PUBLICATIONS

Caravatti, G. et al., "Pyrroloa2, 3-Upyrimidine and Pyrazoloa3, 4-Dupyrimidine Derivatives as Selective Inhibitors of the EGF Receptor Tyrosine Kinase", ACS Symposium Series, 2001 vol. 796 pp. 231-244.

* cited by examiner

Primary Examiner—James O Wilson
Assistant Examiner—Susanna Moore

(57) ABSTRACT

The invention relates to 7H-pyrrolo[2,3-d]-pyrimidine derivatives of formula (I), wherein the symbols and substituents are as defined in the description, to processes for the preparation thereof to pharmaceutical compositions comprising such derivatives and to the use of such derivatives—alone or in combination with one or more other pharmaceutically active compounds —for the preparation of pharmaceutical compositions for the treatment especially of a proliferative disease, such as a tumor.

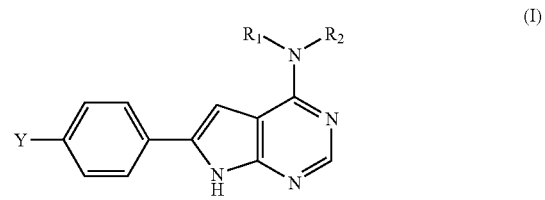

5 Claims, No Drawings

PYRROLO[2,3-D]PYRIMIDINES AS PROTEIN TYROSINE KINASE INHIBITORS

This application is the National Stage of Application No. PCT/EP2005/001635, filed on Feb. 17, 2005. The contents is incorporated herein by reference in its entirety.

This invention relates to 7H-pyrrolopyrimidine derivatives and to the use of those derivatives as medicaments, their pharmaceutical preparation and their process of manufacture.

Accordingly the invention provides compounds of formula I,

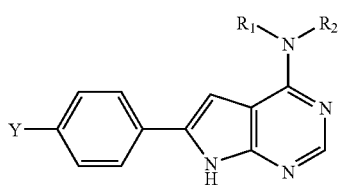

wherein
$R_1$ and $R_2$ are independently hydrogen, halo; or lower alkyl, heterocycle, amino or cycloalkyl all of which may be unsubstituted or substituted;
or $R_1$ and $R_2$ can join together to form an unsubstituted or substituted N-heterocycle;
Y is $(R_3)_n$—X— or $A(R_3)(R_3)C$—;

wherein
X is lower alkyl, amino, amido or carbonyl;
A is hydroxy, amino, halo, or lower alkyl;
$R_3$ is lower alkyl, lower alkoxy, carbonyl, amino, hydroxy, heterocycle or heteroaryl all of which can be unsubstituted or substituted;
n is 1 or 2;
or a pharmaceutically acceptable salt or ester thereof.

Preferably $R_1$ and $R_2$ are independently hydrogen; or lower alkyl, heterocycle, amino or cycloalkyl all of which may be unsubstituted or substituted;
or $R_1$ and $R_2$ can join together to form an unsubstituted or substituted N-heterocycle;
Y is $(R_3)_n$—X— or $A(R_3)(R_3)C$—;

Above and else where in the present description the following terms have the following meanings.

The term "lower" in connection with organic radicals or compounds means a compound or radical which may be branched or unbranched with up to and including 7 carbon atoms, preferably 1-4 carbon atoms.

A lower alkyl group is branched or unbranched and contains 1 to 7 carbon atoms, preferably 1-4 carbon atoms. Lower alkyl represents; for example, methyl, ethyl, propyl, butyl, isopropyl, isobutyl, or tertiary butyl.

A lower alkoxy group is branched or unbranched and contains 1 to 7 carbon atoms, preferably 1-4 carbon atoms. Lower alkoxy represents; for example, methoxy, ethoxy, propoxy, butoxy, isopropoxy, isobutoxy or tertiary butoxy.

Carbonyl is a —C(O)— radical. Unsubstituted carbonyl is —C(O)H and substituted carbonyl is —C(O)$R_3$.

Hydroxy is a —OH radical which is unsubstituted or substituted. Wherein substituted hydroxy is a radical in which the hydrogen has been replaced by a substituent e.g lower alkyl, cycloalkyl or heterocycle.

Halo or halogen represents chloro, fluoro or bromo but can also be iodo.

Heteroaryl is an aromatic cyclic hydrocarbon radical containing from 5 to 18 ring atoms of which one or more, preferably 1 or 2 are heteroatoms selected from 0, N or S. It may be monocyclic or bicyclic heteroaryl. Heterocyclic aryl represents; for example, pyridyl, indoyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl or thienyl, including any said radical substituted.

Cycloalkyl represents a cyclic hydrocarbon radical containing from 3 to 12 ring atoms preferably from 3 to 6 ring atoms. Cycloalkyl represents; for example, cyclopropyl, cyclobutyl, cyclopentyl, cyclohexyl, cycloheptyl or cyclooctyl independently unsubstituted or substituted.

Heterocycle represents a mono-, bi- or tricyclic hydrocarbon radical which is unsaturated or fully or partially saturated and contains one or more, preferably 1 to 3, heteroatoms selected from O, N or S and preferably contains from 3 to 18 ring atoms; for example heterocycle is pyrrolidinyl, tetrahydrothiophenyl, tetrahydrofuranyl, pyranyl, pyrazolidinyl, oxiranyl, dioxanyl, imidazolinyl or imidazolidinyl or especially piperidinyl, morpholinyl or piperazinyl.

N-heterocycle represents a mono-, bi- or tricyclic hydrocarbon radical which is unsaturated or fully or partially saturated and contains at least one nitrogen atom. N-heterocycle can contain one or more, preferably 0, 1, 2 or 3, other heteroatoms selected from O, N or S and preferably contains from 3 to 18 ring atoms; for example a monocyclic hydrocarbon radical with 5 or 6 ring members, at least one of which is a nitrogen atom, which is unsaturated or fully or partially saturated and can contain 1 or 2 other heteroatoms selected from N, O and S. N-heterocycle is for example pyrrolidine, imidazoline, imidazolidine, piperidine, morpholino, or piperazine, especially piperidine, morpholino or piperazine.

Amino is an unsubstituted or substituted —$NH_2$— radical, wherein substituents are for example lower alkyl.

Amido is an unsubstituted or substituted $H_2NC(O)$— radical or unsubstituted or substituted —C(O)NH— radical wherein substituents are for example lower alkyl.

The substituents, e.g. 1-6 preferably 1-3 substituents, on $R_3$ are one or more substituents independently selected from the group consisting of halo, lower alkyl, lower alkoxy, amino, hydroxy and heterocycle; all of which, except halo, are unsubstituted or substituted by one or more substituents e.g 1-6 preferably 1-3 substituents, independently selected from the group consisting of halo, hydroxy, lower alkoxy, amino, lower alkyl and heterocycle; all of which, except halo, are unsubstituted or substituted by one or more substituents e.g 1-6 preferably 1-3 substituents, independently selected from the group consisting of halo, lower alkyl, lower alkoxy, hydroxy and lower alkoxy.

The substituents, e.g. 1-6 preferably 1-3 substituents, on $R_1$ and $R_2$ are one or more substituents independently selected from the group consisting of halo, hydroxy, lower alkyl, lower alkoxy, amino, cycloalkyl, heterocycle and heteroaryl; all of which, except halo, are unsubstituted or substituted by one or more substituents e.g 1-6 preferably 1-3 substituents, independently selected from the group consisting of halo, hydroxy, lower alkyl, lower alkoxy, amino, heterocycle and heteroaryl; all of which, except halo, are unsubstituted or substituted by one or more substituents e.g 1-6 preferably 1-3 substituents, independently selected from the group consisting of halo, hydroxy, lower alkyl and amino.

The compounds of formula I and as listed below are herein referred to as agents of the invention.

Pharmaceutically acceptable salts of the acidic agents of the Invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

For isolation or purification purposes it is also possible to use pharmaceutically unacceptable salts, for example picrates or perchlorates. Only salts that are pharmaceutically acceptable and non-toxic (at the appropriate dosages) are used therapeutically and those salts are therefore preferred.

The Agents of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an unsubstituted or substituted lower alkanoic acid or an arylcarboxylic acid.

The compounds of formula I exhibit valuable pharmacological properties in mammal and are particularly useful as inhibitors of Bcr-Abl In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which transforms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl prevent the kinase from activating mitogenic and anti-apoptotic pathways (e.g. P-3 kinase and STAT5), leading to the death of the BCR-ABL phenotype cells and thereby providing an effective therapy against CML. An agent of the invention, as a Bcr-Abl inhibitor, are thus especially appropriate for the therapy of diseases related to Bcr-Abl overexpression, especially leukemias, such as leukemias, e.g. CML or ALL.

The compounds of formula I have valuable pharmacological properties, as described hereinbefore and hereinafter.

The efficacy of the compounds of the invention as inhibitors of c-Abl, Bcr-Abl, Raf and VEGF-receptor tyrosine kinase activity can be demonstrated as follows:

Test for activity against c-Abl protein tyrosine kinase. The test is conducted as a filter binding assay as follows: The His-tagged kinase domain of c-Abl is cloned and expressed in the baculovirus/Sf9 system as described by Bhat et al., J. Biol. Chem. 272, 16170-5 (1997). A protein of 37 kD (c-Abl kinase) is purified by a two-step procedure over a cobalt metal chelate column followed by an anion exchange column with a yield of 1-2 mg/L of Sf9 cells. The purity of the c-Abl kinase is >90% as judged by SDS-PAGE after Coomassie blue staining. The assay contains: c-Abl kinase (50 ng), 20 mM Tris.HCl, pH 7.5, 10 mM $MgCl_2$, 10 µM $Na_3VO_4$, 1 mM DTT and 0.06 µCi/assay [$\gamma^{33}$ P]-ATP (5 µM ATP) using 30 µg/mL poly-Ala,Glu,Lys,Tyr-6:2:5:1 (Poly-AEKY, Sigma P1152) in the presence of 1% DMSO, total volume of 30 µL. Reactions are terminated by adding 10 µL of 250 mM EDTA, and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). The $IC_{50}$-values that can be found with compounds of formula I are in the range of 1 to 10,000 nM, preferably in the range of 1 to 1000 nm and most preferably in the range of 1 to 100 nM.

Test for activity against Bcr-Abl. The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institute, Boston, Mass., USA). The cells express the fusion Bcr-Abl protein with a constitutively active Abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of $2 \times 10^6$ cells per vial in freezing medium (95% FCS, 5% DMSO (SIGMA)). After thawing, the cells are used during maximally 10-12 passages for the experiments.

For cellular assays, compounds are dissolved in DMSO and diluted with complete medium to yield a starting concentration of 10 µM followed by preparation of serial 3-fold dilutions in complete medium. 200,000 32D-Bcr/Abl cells in 50 µL complete medium are seeded per well in 96 well round bottom tissue culture plates. 50 µL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 µg/mL aprotinin and 80 µg/mL leupeptin) and either used immediately for the ELISA or stored frozen in the plates at −20° C. until usage.

Black ELISA plates (Packard HTRF-96 black plates) are precoated over night at 4° C. with 50 ng/well of the rabbit polyclonal anti-abl-SH3 domain Ab 06-466 from Upstate in 50 µL PBS. After washing 3 times with 200 µL/well PBS containing 0.05% Tween20 (PBST) and 0.5% TopBlock (Juro), residual protein binding sites are blocked with 200 µL/well PBST, 3% TopBlock for 4 h at room temperature followed by incubation with 50 µL lysates of untreated or compound-treated cells (20 µg total protein per well) for 3-4 h at 4° C. After 3 washings, 50 µL/well anti-phosphotyrosine Ab PY20(AP) labeled with alkaline phosphatase (Zymed) diluted to 0.2 µg/mL in blocking buffer is added and incubated over night (4° C.). For all incubation steps the plates are covered with plate sealers (Costar). Finally, the plates are washed another three times with washing buffer and once with deionized water before addition of 90 μL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count). The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the IC50 and IC90 are determined from the dose response curves by graphical extrapolation. The IC50-values that can be found with compounds of formula I are in the range of 1 to 10,000 nM, preferably in the range of 1 to 5000 nM, even more preferably in the range of 1 to 1000 nM.

Test for activity against mutant Bcr-Abl: The activity of compounds on the M351T mutant Bcr-Abl kinase activity is assessed as described above, except that 32Dcl3 cells transfected with mutant Bcr-Abl in place of p210 Bcr-Abl are utilised.

c-Raf-1 protein kinase assay: Recombinant c-Raf-1 protein is obtained by triple infection of Sf21 cells with GST-c-Raf-1 recombinant baculovirus together with v-Src and v-Ras recombinant baculoviruses that are required for active c-Raf-1 kinase production (Williams et al., PNAS 1992; 89:2922-6). Active Ras (v-Ras) is required to recruit c-Raf-1 to the cell membrane and v-Src to phosphorylate c-Raf-1 to fully activate it. Cells are seeded at $2.5\times10^7$ cells per 150 mm dish and allowed to attach to a 150 mm dish for 1 hr at RT. Media (SF900II containing 10% FBS) is aspirated and recombinant baculovirus GST-c-Raf-1, v-Ras and v-Src are added at MOI of 3.0, 2.5 and 2.5, respectively, in a total volume of 4-5 mL. Cells are incubated for 1 hr at RT and then 15 mL of medium is added. Infected cells are incubated for 48-72 hr at 27° C. Infected Sf21 cells are scraped and collected into a 50 mL tube and centrifuged for 10 min at 4° C. at 1100 g in a Sorvall centrifuge. The cell pellet is washed once with ice cold PBS and lysed with 0.6 mL lysis buffer per $2.5\times10^7$ cells. Complete lysis of cells is achieved after 10 min on ice with occasional pipetting. The cell lysates are centrifuged for 10 min at 4° C. at 14,500 g in a Sorvall centrifuge with SS-34 rotor and the supernatant is transferred to a fresh tube and stored at −80° C. c-Raf-1 is purified from cell lysates using 100 μL of packed glutathione-sepharose 4B beads equilibrated in ice cold PBS per $2.5\times10^7$ cells. GST-c-Raf-1 is allowed to bind to the beads at 4° C. for 1 hr with rocking. Bound GST-c-Raf-1 with beads is transferred to a column. The column is washed once with lysis buffer and twice with ice cold Tris buffered saline. Ice cold elution buffer is added and column flow is stopped to allow the free glutathione to disrupt the interaction of GST-c-Raf-1 with glutathione sepharose beads. Fractions (1 mL) are collected into pre-chilled tubes. Each tube contains 10% glycerol (final concentration) to maintain kinase activity during freeze thaw cycles. Purified fractions of GST-c-Raf-1 kinase protein are stored at −80° C.

IκB is used as substrate for the c-Raf-1 kinase. IκB is expressed in bacteria as a His-tagged protein BL21. LysS bacteria containing the IκB plasmid are grown to an OD600 of 0.6 in LB medium, then induced to express the IκB with IPTG (final concentration of 1 mM) for 3 hrs at 37° C. and then bacteria are lysed by sonication (microtip limit setting for 3 times at 1 min each in sonication buffer [50 mM Tris pH 8.0, 1 mM DTT, 1 mM EDTA] and centrifuged at 10,000 g for 15 min. The supernatant is mixed with ammonium sulfate to give a final concentration of 30%. This mixture is rocked for 15 min at 4 C then spun at 10,000 g for 15 min. The pellet is resuspended in binding buffer (Novagen) containing 10 mM BSA. This solution is applied to Ni-agarose (Novagen) and washed according to the Novagen manual. IκB is eluted from the column using elution buffer (0.4 M imidazole, 0.2 M NaCl, 8 mM Tris pH 7.9). Fractions containing protein are dialysed in 50 mM Tris pH 8, 1 mM DTT. The activity of c-Raf-1 protein kinase is assayed in the presence or absence of inhibitors, by measuring the incorporation of $^{33}P$ from $[\gamma^{33}P]$ATP into IκB. The assay is carried out in 96-well plates at ambient temperature for 60 min. It contains (total volume of 30 μL): c-Raf-1 kinase (400 ng), 25 mM Tris.HCl, pH 7.5, 5 mM $MgCl_2$, 5 mM $MnCl_2$, 10 μM $Na_3VO_4$, 1 mM DTT and 0.3 μCi/assay $[\gamma^{33}P]$-ATP (10 μM ATP) using 600 ng IκB in the presence of 1% DMSO. Reactions are terminated by adding 10 μL of 250 mM EDTA and 30 μL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed 4× on a shaker with 0.5% $H_3PO_4$, once with ethanol. Membranes are counted after drying at ambient temperature, mounting in Packard TopCount 96-well frame, and addition of 10 μL/well of Microscint™ (Packard). The % inhibition, at 10 M, values that can be found with compounds of formula I are in the range of 10 to 100%, preferably in the range of 25 to 100%, even more preferably in the range of 50 to 100%.

Test for activity against VEGF-receptor tyrosine kinase. The test is conducted using Flt-3 VEGF-receptor tyrosine kinase. The detailed procedure is as follows: 30 μL kinase solution (10 ng of the kinase domain of Flt-3, Shibuya et al., Oncogene 5, 519-24[1990]) in 20 mM Tris.HCl pH 7.5, 3 mM manganese dichloride ($MnCl_2$), 3 mM magnesium chloride ($MgCl_2$), 10 μM sodium vanadate, 0.25 mg/mL polyethyleneglycol (PEG) 20000, 1 mM dithiothreitol and 3 μg/μL poly(Glu,Tyr) 4:1 (Sigma, Buchs, Switzerland), 8 μM $[^{33}P]$-ATP (0.2 μCi), 1% DMSO, and 0 to 100 μM of the compound to be tested are incubated together for 10 minutes at room temperature. The reaction is then terminated by the addition of 10 μL 0.25 M ethylenediaminetetraacetate (EDTA) pH 7. Using a multichannel dispenser (LAB SYSTEMS, USA), an aliquot of 20 μL is applied to a PVDF (=polyvinyl difluoride) Immobilon P membrane (Millipore, Bedford, USA), through a Gibco-BRL microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 μL Microscint®(β-scintillation counter liquid). $IC_{50}$-values are determined by linear regression analysis of the percentages for the inhibition of each compound in at least four concentrations (as a rule 0.01, 0.1, 1.0 and 10 μmol). The $IC_{50}$-values that can be found with compounds of formula 1 are in the range of 1 to 10,000 nM, preferably in the range of 1 to 5000 nM, even more preferably in the range of 1 to 1000 nM and most preferably in the range of 1 to 500 nM.

The inhibition of VEGF-induced KDR-receptor autophosphorylation can be confirmed with a further in vitro experiment in cells: transfected CHO cells, which permanently express human VEGF receptor (KDR), are seeded in complete culture medium with 10% fetal calf serum (FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/mL). After a further five minute incubation at 37° C., the cells are washed twice with ice-cold PBS (phosphate-buffered saline) and immediately lysed in 100 μL lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an anti-phosphotyrosine antibody coupled with alkaline phosphatase (PY20: AP from Transduction Laboratories). The plates are washed again and the binding of the antiphosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the IC50 (effective dose for 50% inhibition). The $IC_{50}$-values that can be found with compounds of formula I are in the range of 1 to 10,000 nM, preferably in the range of 1 to 500 nM, even more preferably in the range of 1 to 2000 nM. The % inhibition values that can be found with compounds of formula I are in the range of 10 to 100%, preferably in the range of 30 to 100%, even more preferably in the range of 50 to 100%.

An agent of the invention inhibits besides BCR-Abl, c-Abl also to varying degrees other tyrosine kinases involved in signal transduction which are mediated by trophic factors, for example Raf kinase, Arg, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase, using known procedures.

On the basis of these studies, an agent of the invention shows therapeutic efficacy especially against disorders dependent on protein kinase deregulation, especially leukemias and proliferative diseases.

An agent of the invention is also effective against a number of diseases for example number of diseases associated with protein kinase deregulation especially neoplastic diseases e.g. solid tumors, leukemias and other "liquid tumors", especially those expressing c-kit, KDR, Flt-1 or Flt-3, such as especially breast cancer, cancer of the colon, lung cancer (especially small-cell lung cancer), cancer of the prostate or Kaposi's sarcoma.

An agent of the invention also inhibits the growth of tumours and is especially suited to preventing the metastatic spread of tumors and the growth of micrometastases, for example Raf kinase, Arg, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

An agent of the invention is also effective against diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmnune diseases, diabetes, endometriosis, chronic asthma.

An agent of the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

The present invention relates especially also to the use of an agent of the invention, or a pharmaceutically acceptable salt thereof, especially an agent of the invention which is said to be preferred, or a pharmaceutically acceptable salt thereof, for the preparation of a pharmaceutical composition for the therapeutic and also prophylactic management of one or more of the diseases mentioned hereinabove, especially a neoplastic disease, in particular if the disease responds to an inhibition of a protein tyrosine kinase, especially to inhibition of Bcr-Abl.

In accordance with the foregoing the present invention also provides in a further series of embodiments:

A. A method of inhibiting Bcr-Abl in a subject (i.e., a mammal, especially a human) in need of such treatment which method comprises administering to said subject an effective amount of an agent of the invention, or a method of treating any of the above mentioned conditions, particularly a method of treating a proliferative disease or condition, or alleviating one or more symptoms of any of the above mentioned conditions.

B. An agent of the invention for use as a pharmaceutical, or for use in the prevention, amelioration or treatment of any disease or condition as described above, e.g., a proliferative disease or condition.

C. A pharmaceutical composition comprising an agent of the invention in association with a pharmaceutically acceptable diluent or carrier, e.g., for use as an anti-proliferative agent or for use in the prevention, amelioration or treatment of any disease or condition as described above, e.g. a proliferative disease or condition.

D. Use of an agent of the invention in the manufacture of a medicament for use as an anti-proliferative agent or for use in the prevention, amelioration or treatment of any disease or condition as described above, e.g., a proliferative disease or condition.

An agent of the invention can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. An agent of the invention can besides or in addition be administered especially for tumor therapy, such as leukemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

An agent of the invention can be administered alone or in combination with one or more other therapeutic agents. Such therapeutic agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Nati. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632 and KRN-633;

anti-angiogenic compounds having another mechanism of action than decreasing the protein kinase activity include, but are not limited to e.g. thalidomide (THALOMID), celecoxib (Celebrex), SU5416 and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, eg. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin ™), rituximab (Rituxan®), PRO64553 (anti-CD40) and 2C4 Antibody.

For the treatment of AML, compounds of formula I can be used in combination with standard leukemia therapies, especially in combination with therapies used for the treatment of AML. In particular, compounds of formula I can be administered in combination with e.g. farnesyltransferase inhibitors and/or other drugs used for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with an agent of the invention, can be prepared and administered as described in the art such as in the documents cited above.

Preference is given to compounds of formula I wherein

A is preferably hydroxy, amino or lower alkyl;

$R_1$ and $R_2$ are preferably and independently hydrogen; or lower alkyl, heterocycle, amino or cycloalkyl all of which may be unsubstituted or substituted;

or $R_1$ and $R_2$ can join together to form an unsubstituted or substituted N-heterocycle.

$R_3$ is prefereably lower alkyl, lower alkoxy, amino, hydroxy, heterocycle or heteroaryl all of which may be unsubstituted or substituted.

$R_1$ and $R_2$ are preferably unsubstituted or substituted by one or more substituents e.g 1-6 preferably 1-3 substituents, independently selected from the group consisting of hydroxy, lower alkyl, lower alkoxy, amino, cycloalkyl, heterocycle and heteroaryl; all of which are unsubstituted or substituted by one or more substituents e.g 1-6 preferably 1-3 substituents, independently selected from the group consisting of lower alkyl, lower alkoxy, amino, heterocycle and heteroaryl; all of which are unsubstituted or substituted by one or more substituents e.g 1-6 preferably 1-3 substituents, independently selected from the group consisting of hydroxy and lower alkyl.

$R_3$ is prefereably unsubstituted or substituted by e.g. 1-6 preferably 1-3 substituents, independently selected from the group consisting of lower alkyl, lower alkoxy, amino, hydroxy and heterocycle; all of which are unsubstituted or substituted by one or more substituents e.g 1-6 preferably 1-3 substituents, independently selected from the group consisting of hydroxy, amino, lower alkyl, lower alkoxy and heterocycle; all of which are unsubstituted or substituted by one or more substituents e.g 1-6 preferably 1-3 substituents, independently selected from the group consisting of lower alkyl, lower alkoxy, hydroxy and lower alkoxy.

In a preferred embodiment the invention provides compounds of formula I wherein $R_1$ and $R_2$ are independently hydrogen, halo; or lower alkyl, heterocycle selected from pyrrolidine, tetrahydrothiophene, tetrahydrofuran, piperidine, pyran, pyrazolidine, oxirane, dioxane, imidazoline, imidazolidine, morpholino and piperazine, amino or cycloalkyl selected from cyclopropyl, cyclobutyl, cyclopentyl, cyclohexyl, cycloheptyl and cyclooctyl; all of which may be unsubstituted or substituted;

or $R_1$ and $R_2$ can join together to form an unsubstituted or substituted N-heterocycle selected from pyrrolidine, imidazoline, imidazolidine, piperidine, pyran, morpholino, and piperazine;

Y is $(R_3)_n$—X— or of formula II;

wherein

X is lower alkyl, amino, amido or carbonyl;

A is hydroxy, amino, halo, or lower alkyl;

$R_3$ is lower alkyl, lower alkoxy, carbonyl, amino, hydroxy, heterocycle selected from pyrrolidine, tetrahydrothiophene, tetrahydrofuran, piperidine, pyran, pyrazolidine, oxirane, dioxane, imidazoline, imidazolidine, morpholino and piperazine, or heteroaryl selected from pyridyl, indoyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl and thienyl, all of which may be unsubstituted or substituted;

n is 1 or 2;

The substituents, e.g. 1-6 preferably 1-3 substituents, on $R_3$ are one or more substituents independently selected from the group consisting of halo, lower alkyl, lower alkoxy, amino, hydroxy and heterocycle selected from pyrrolidine, tetrahydrothiophene, tetrahydrofuran, piperidine, pyran, pyrazolidine, oxirane, dioxane, imidazoline, imidazolidine, morpholino and piperazine; all of which, except halo, are unsubstituted or substituted by one or more substituents e.g 1-6 preferably 1-3 substituents, independently selected from the group consisting of halo, hydroxy, lower alkoxy, amino, lower alkyl and heterocycle selected from pyrrolidine, tetrahydrothiophene, tetrahydrofuran, piperidine, pyran, pyrazolidine, oxirane, dioxane, imidazoline, imidazolidine, morpholino and piperazine; all of which, except halo, are unsubstituted or substituted by one or more substituents e.g 1-6 preferably 1-3 substituents, independently selected from the group consisting of halo, lower alkyl, lower alkoxy, hydroxy and lower alkoxy.

The substituents, e.g. 1-6 preferably 1-3 substituents, on $R_1$ and $R_2$ are one or more substituents independently selected from the group consisting of halo, hydroxy, lower alkyl, lower alkoxy, amino, cycloalkyl selected from cyclopropyl, cyclobutyl, cyclopentyl, cyclohexyl, cycloheptyl and cyclooctyl, heterocycle selected from pyrrolidine, tetrahydrothiophene, tetrahydrofuran, piperidine, pyran, pyrazolidine, oxirane, dioxane, imidazoline, imidazolidine, morpholino and piperazine and heteroaryl selected from pyridyl, indoyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl and thienyl, all of which, except halo, are unsubstituted or substituted by one or more substituents e.g 1-6 preferably 1-3 substituents, independently selected from the group consisting of halo, hydroxy, lower alkyl, lower alkoxy, amino, heterocycle selected from pyrrolidine, tetrahydrothiophene, tetrahydrofuran, piperidine, pyran, pyrazolidine, oxirane, dioxane, imidazoline, imidazolidine, morpholino and piperazine and heteroaryl selected from pyridyl, indoyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl and thienyl, all of which, except halo, are unsubstituted or substituted by one or more substituents e.g 1-6 preferably 1-3 substituents, independently selected from the group consisting of halo, hydroxy, loweralkyl and amino.

or a pharmaceutically acceptable salt or ester thereof.

In another preferred embodiment the invention provides compounds of formula I wherein $R_1$ and $R_2$ are independently hydrogen, lower alkyl, cycloalkyl, hydroxy lower alkyl, lower alkoxy-lower alkyl, lower alkyl-amino-lower alkyl, heterocycle-lower alkyl;

or $R_1$ and $R_2$ can join together to form a N-heterocycle or lower alkyl-N-heterocycle;

Y is $(R_3)_n$—X— or $A(R_3)(R_3)C$—;

wherein

X is lower alkyl or carbonyl;

A is hydroxy;

n is 1;

$R_3$ is lower alkyl, lower alkoxy, amino, heterocycle, heteroaryl, lower alkyl-heterocycle, lower alkyl-amino-lower alkyl, heterocycle-lower alkyl-amino, lower alkyl-amino, hydroxy-lower alkyl-amino, amino substituted by lower alkoxy-lower alkyl and lower alkyl;

or a pharmaceutically acceptable salt or ester thereof.

In an even further preferred embodiment the invention also provides compounds of formula I wherein R₁ and R₂ are independently hydrogen, methyl, ethyl, propyl, cyclopropyl, hydroxy-propyl, dimethylamino-ethyl, morpholinyl-propyl, methoxy-ethyl, pyrrolidinyl-propyl;

or R₁ and R₂ can join together to form a piperazinyl or methyl-piperazinyl, preferably N-methyl-piperazinyl;

Y is (R₃)ₙ—X— or A(R₃)(R₃)C—;

wherein

X is CH₂ or —C(O)—;

A is hydroxy;

n is 1;

R₃ is methyl, ethyl, butoxy, morpholinyl, piperazinyl, pyrrolyl, tetrazoyl, imidazoyl, methyl-piperazinyl, diethyl-amino-propyl, morpholino-propyl-amino, methyl-amino, hydroxy-propyl-amino, (methoxy-ethyl)methyl-amino;

or a pharmaceutically acceptable salt or ester thereof.

In a yet even further preferred embodiment the invention provides compounds of formula I wherein R₁ and R₂ are independently hydrogen, methyl, ethyl or propyl;

Y is (R₃)ₙ—X— or A(R₃)(R₃)C—;

wherein

X is CH₂ or —C(O)—;

A is hydroxy;

n is 1

R₃ is methyl, piperazinyl, morpholino or imidazoyl all of which may be unsubstituted or substituted;

wherein the substituents e.g. 1-6 preferably 1-3 and most preferably 1 on R₃ are methyl;

or a pharmaceutically acceptable salt or ester thereof.

In particular the invention includes a compound selected from:

Methyl-{6-[4-(4-methyl-piperazin-1-ylmethyl)phenyl]-7H-pyrrolo[2,3-d]pyrimidin-4-yl}-propylamine;

[4-(4-Methylamino-7H-pyrrolo[2,3-d]pyrimidin-6-yl)-phenyl]-morpholin-4-yl-methanone;

[4-(4-Dimethylamino-7H-pyrrolo[2,3-d]pyrimidin-6-yl)-phenyl]-(4-methyl-piperazin-1-yl)-methanone;

Dimethyl-{6-[4-(4-methyl-piperazin-1-ylmethyl)-phenyl]-7H-pyrrolo[2,3-d]pyrimidin-4-yl}-amine;

N-(3-Diethylamino-propyl)-4-(4-dimethylamino-7H-pyrrolo[2,3-d]pyrimidin-6-yl)-benzamide;

[4-(4-Dimethylamino-7H-pyrrolo[2,3-d]pyrimidin-6-yl)-phenyl]-morpholin-4-yl-methanone;

4-(4-Dimethylamino-7H-pyrrolo[2,3-d]pyrimidin-6-yl)-N-(3-morpholin-4-yl-propyl)-benzamide;

(4-Methyl-piperazin-1-yl)-{4-[4-(4-methyl-piperazin-1-yl)-7H-pyrrolo[2,3-d]pyrimidin-6-yl]-phenyl}-methanone;

4-(4-Methyl-piperazin-1-yl)-6-[4-(4-methyl-piperazin-1-ylmethyl)-phenyl]-7H-pyrrolo[2,3-d]pyrimidine;

{4-[4-(Ethyl-methyl-amino)-7H-pyrrolo[2,3-d]pyrimidin-6-yl]-phenyl}-(4-methyl-piperazin-1-yl)-methanone;

[4-(4-Isopropylamino-7H-pyrrolo[2,3-d]pyrimidin-6-yl)-phenyl]-(4-methyl-piperazin-1-yl)-methanone;

[4-(4-Methylamino-7H-pyrrolo[2,3-d]pyrimidin-6-yl)-phenyl]-(4-methyl-piperazin-1-yl)-methanone;

Isopropyl-{6-[4-(4-methyl-piperazin-1-ylmethyl)-phenyl]-7H-pyrrolo[2,3-d]pyrimidin-4-yl}-amine;

Ethyl-methyl-{6-[4-(4-methyl-piperazin-1-ylmethyl)-phenyl]-7H-pyrrolo[2,3-d]pyrimidin-4-yl}-amine;

{4-[4-(3-Hydroxy-propylamino)-7H-pyrrolo[2,3-d]pyrimidin-6-yl]-phenyl}-(4-methyl-piperazin-1-yl)-methanone;

Methyl-{6-[4-(4-methyl-piperazin-1-ylmethyl)-phenyl]-7H-pyrrolo[2,3-d]pyrimidin-4-yl}-amine;

(4-Methyl-piperazin-1-yl)-[4-(4-propylamino-7H-pyrrolo[2,3-d]pyrimidin-6-yl)-phenyl]-methanone;

{6-[4-(4-Methyl-piperazin-1-ylmethyl)-phenyl]-7H-pyrrolo[2,3-d]pyrimidin-4-yl}-propyl-amine;

Methyl-{6-[4-(4-methyl-piperazin-1-ylmethyl)-phenyl]-7H-pyrrolo[2,3-d]pyrimidin-4-yl}-propyl-amine;

[4-(4-Cyclopropylamino-7H-pyrrolo[2,3-d]pyrimidin-6-yl)-phenyl]-(4-methyl-piperazin-1-yl)-methanone;

N-Methyl-4-(4-methylamino-7H-pyrrolo[2,3-d]pyrimidin-6-yl)-benzamide;

{4-[4-(2-Dimethylamino-ethylamino)-7H-pyrrolo[2,3-d]pyrimidin-6-yl]-phenyl}-(4-methyl-piperazin-1-yl)-methanone;

N, N-Dimethyl-N'-{6-[4-(4-methyl-piperazin-1-ylmethyl)-phenyl]-7H-pyrrolo[2,3-d]pyrimidin-4-yl}-ethane-1,2-di-amine;

[6-(4-Imidazol-1-ylmethyl-phenyl)-7H-pyrrolo[2,3-d]pyrimidin-4-yl]-dimethyl-amine;

Dimethyl-{6-[4-(1H-pyrrol-2-ylmethyl)-phenyl]-7H-pyrrolo[2,3-d]pyrimidin-4-yl}-amine;

[6-(4-Butoxymethyl-phenyl)-7H-pyrrolo[2,3-d]pyrimidin-4-yl]-dimethyl-amine;

Dimethyl-[6-(4-tetrazol-1-ylmethyl-phenyl)-7H-pyrrolo[2,3-d]pyrimidin-4-yl]-amine;

3-[4-(4-Dimethylamino-7H-pyrrolo[2,3-d]pyrimidin-6-yl)-benzylamino]-propan-1-ol;

[6-(4-{[(2-Methoxy-ethyl)-methyl-amino]-methyl}-phenyl)-7H-pyrrolo[2,3-d]pyrimidin-4-yl]-dimethyl-amine;

3-{4-[4-(3-Morpholin-4-yl-propylamino)-7H-pyrrolo[2,3-d]pyrimidin-6-yl]-phenyl}-pentan-3-ol;

2-(4-{4-[Bis-(2-methoxy-ethyl)-amino]-7H-pyrrolo[2,3-d]pyrimidin-6-yl}-phenyl)-propan-2-ol;

3-(4-{4-[Bis-(2-methoxy-ethyl)-amino]-7H-pyrrolo[2,3-d]pyrimidin-6-yl}-phenyl)-pentan-3-ol;

3-{4-[4-(3-Pyrrol-1-yl-propylamino)-7H-pyrrolo[2,3-d]pyrimidin-6-yl]-phenyl}-pentan-3-ol;

2-[4-(4-Dimethylamino-7H-pyrrolo[2,3-d]pyrimidin-6-yl)-phenyl]-propan-2-ol;

2-[4-(4-Methylamino-7H-pyrrolo[2,3-d]pyrimidin-6-yl)-phenyl]-propan-2-ol;

or a pharmaceutically acceptable salt or ester thereof.

Agents of the Invention may be prepared by processes as described below:

a) reduction of a compound of formula II

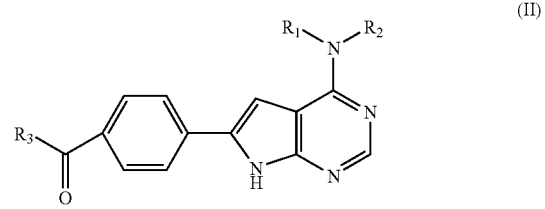

(II)

For example with a reducing agent e.g lithium aluminum hydride preferably in an inert solvent such as THF and advantageously under an inert atmosphere such as nitrogen.

b) coupling a compound of formula VII

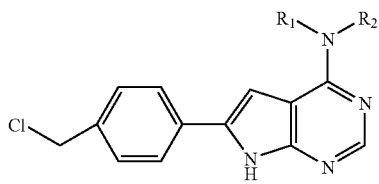
(VII)

With a compound of formula VIIa,

 (VIIa)

wherein R₃ of formula VIIa is unsubstituted or substituted amino, heterocycle or heteroaryl. For example in an inert solvent such as butanol and advantageously in the presence of NaI preferably at an increased temperature e.g reflux.

c) for compounds wherein Y in formula I is A(R₃)(R₃)C—. Conversion of a compound of formula XII

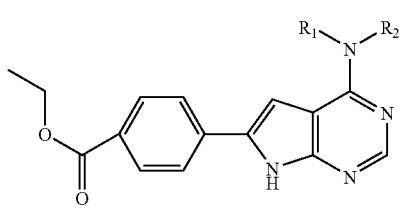
(XII)

For example with an organometallic compound e.g a compound of formula XIII

R₃—MgZ (XIII)

wherein Z is a halide and R₃ is a previously defined, e.g. ethylmagnesium bromide. For example in an inert solvent such as THF and advantageously at a reduced temperature and also advantageously under an inert atmosphere.

The starting material of formula II may be prepared by hydrolysis of a compound of formula VI

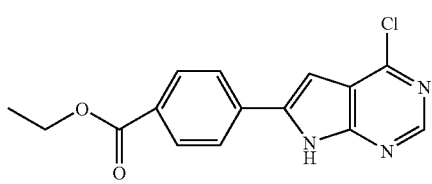
(VI)

to yield a compound of formula V.

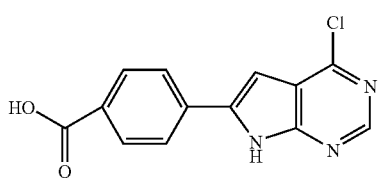
(V)

For example with LiOH and H₂O in a solvent such as MeOH. Compound of formula VI may be prepared for example as set out on pages 70-71 in WO 97/02266.

a compound of formula V is then coupled with a compound of fomula VIIa

 (VIIa)

wherein R₃ of formula VIIa is unsubstituted or substituted amino, heterocycle or heteroaryl to yield a compound of formula III

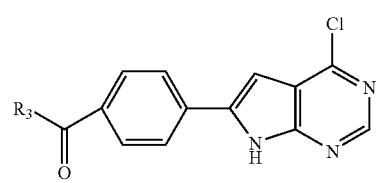
(III)

For example first forming the activated acid of a compound of formula V for example treating with oxalyl chloride advantageously in an inert solvent and preferably under an inert atmosphere. The activated acid is then treated with VIIa advantageously in the presence of a base such as triethylamine preferably at a reduced temperature.

compound of formula III is then coupled with a compound of formula IV

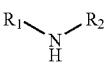 (IV)

To form the desired starting material of formula II

For example in an inert solvent such as butanol and advantageously at an increased temperature e.g. 50-120° C.

The starting material of formula Vii may be prepared by treating a compound of formula VI

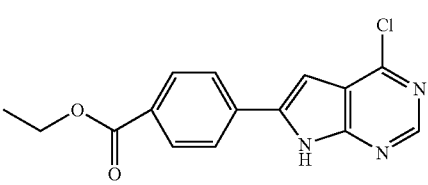
(VI)

with a compound of formula XI

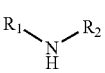 (XI)

To yield a compound of formula IX

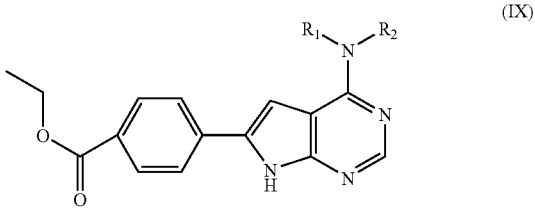

advantageously in a sealed tube and preferably at an elevated temperature. Compound of formula VI may be prepared for example as set out on pages 70-71 in WO 97/02266.

Compound of formula 10 is reduced to yield a compound of formula VIII

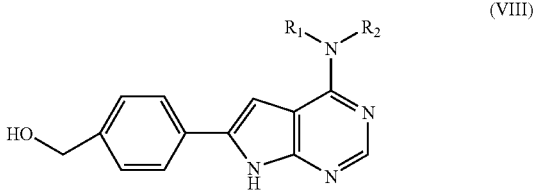

for example with a reducing agent e.g. lithium aluminum hydride in an inert solvent such as THF advantageously at an elevated temperature e.g. 30-70° C. and preferably under an inert atmosphere such as argon.

Compound of formula VIII is then converted to the desired starting material of formula VII. For example by treating a compound of formula VIII with reagent such as thionyl chloride in an inert solvent such as toluene and advantageously at a reduced temperature e.g. 10-(−20° C.)

Method C

The starting material of formula XII may be prepared by treating a compound of formula VI

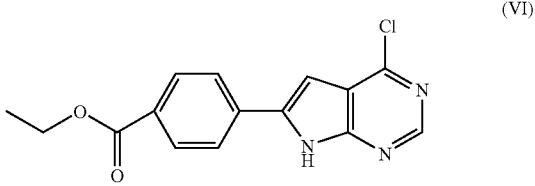

with a compound of formula XI

For example in an inert solvent such as butanol advantageously at an elevated temperature e.g. 60-100C. Compound of formula VI may be prepared for example as set out on pages 70-71 in WO 97/02266.

The invention relates also to processes and to the use of an agent of the invention, or a pharmaceutically acceptable salt thereof, for the preparation of pharmaceutical compositions which comprise an agent of the invention, or a pharmaceutically acceptable salt thereof, as active component (active ingredient).

If desired, the said pharmaceutical compositions may also contain further active components, for example cytostatics, and/or may be used in combination with known therapeutic processes, for example the administration of hormones or radiation.

Preference is given for a pharmaceutical composition which is suitable for administration to a warm-blooded animal, especially humans or commercially useful mammals suffering from a disease which responds to an inhibition of a protein tyrosine kinase, especially to an inhibition of BCR-Abl etc., comprising an effective quantity of an agent of the invention for the inhibition of a protein tyrosine kinase, especially for the inhibition Bcr-Abl, or a pharmaceutically acceptable salt thereof, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases an agent of the invention, or a pharmaceutically acceptable salt thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of a protein tyrosine kinase, especially to inhibition of Bcr-Abl, especially a corresponding neoplastic disease. An agent of the invention, or pharmaceutically acceptable salts thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of an agent of the invention, or a pharmaceutically acceptable salt thereof, especially an agent of the invention which is said to be preferred, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, preferably a disease which responds to an inhibition of a protein tyrosine kinase, especially to a inhibition of Bcr-Abl, especially a neoplastic disease, in particular if the said disease responds to an inhibition of a protein tyrosine kinase, especially to inhibition of Bcr-Abl.

The invention is further described in the following non-limiting examples.

Experimental Section

The preparation of 7H-pyrrolopyrimidine derivatives and their intermediates are illustrated in the reaction schemes below and described in the examples 1-35.

Abbreviations:
DMF: N,N-Dimethyl formamide
HCl: Hydrochloric acid
NaOH: Sodium hydroxide
LIOH: Lithium hydroxide
THF: Tetrahydrofuran

EXAMPLES

Example 1

(4-Methylpiperazin-1-yl)-{4-[-(methyl-propyl-amino)-7H-pyrrolo[2,3-d]pyrimidin-6-yl]-phenyl}-methanone (43 mg, 0.11 mmol) is dissolved in THF (1 mL) at room temperature and LiAlH$_4$ (17 mg, 0.44 mmol) is added in small portions under an argon atmosphere. The reaction is then allowed to stir for 2 h and worked up by careful addition of ethyl acetate and H$_2$O. The phases are separated and the aqueous layer is repeatedly extracted with ethyl acetate. Combined organic extracts are washed with brine and dried over MgSO$_4$. After filtration and removal of the solvents in vacuo methyl-{6-[4-(4-methyl-piperazin-1-ylmethyl)phenyl]-7H-pyrrolo[2,3-d]pyrimidin-4-yl}-propylamine is obtained as a white powder. $C_{22}H_{26}N_6$: M+H=379.2; $^1$H-NMR (400 MHz, DMSO-$d_6$): 12.01 (s, 1H, NH), 8.15 (s, 1H), 7.80 (d, 2H), 7.34 (d, 2H), 6.99 (s, 1H), 3.72-3.65 (m, 2H), 3.41 (s, 2H), 2.59-2.21 (m, 8H), 2.17 (s, 3H), 1.78-1.59 (m, 2H)1.71-1.60 (m, 2H), 0.96 (t, 3H). m. p.=220-221° C.

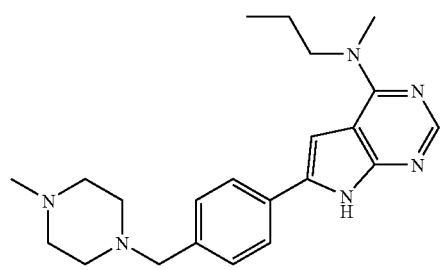

The starting material is obtained as follows:

Example 1

Step 1: 4-(4-Chloro-7H-pyrrolo[2,3-d]pyrimidin-6-yl)-benzoic acid

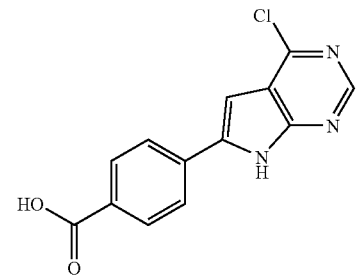

4-(4-Chloro-7H-pyrrolo[2,3]pyrimidin-6-yl)-benzoic acid ethyl ester (WO 97/02266, 10.0 g, 33.14 mmol) is suspended in MeOH (70 mL) and treated with a solution of LiOH×H$_2$O (3.48 g, 82.55 mmol) in H$_2$O (55 mL) at room temperature and stirred for 16 h. The reaction mixture was then acidified with 4 N aqueous HCl solution to pH 2 and the precipitated product is isolated by filtration, washed with cold H$_2$O and dried in vacuo at 60° C. to give the title compound as a white powder. $C_{13}H_8ClN_3O_2$: M+H=274.1; $^1$H-NMR (400 MHz, DMSO-$d_6$): 13.19 (s, 1H), 8.61 (s, 1H), 8.17 (d, 2H), 8.01 (d, 2H), 7.22 (s, 1H).

Example 1

Step 2: 4-(4-Chloro-7H-pyrrolo[2,3-d]pyrimidin-6-yl)-phenyl]-(4-methyl-piperazin-1-yl)-methanone

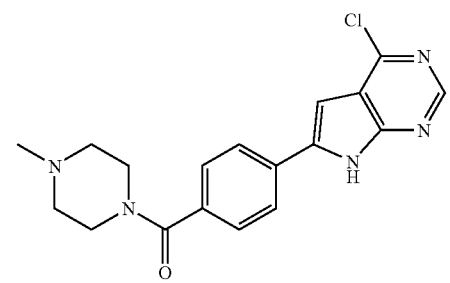

4-(4-Chloro-7-H-pyrrolo[2,3-d]pyrimidin-6-yl)-benzoic acid (500 mg, 1.86 mmol) is suspended in dry THF (20 mL) under an argon atmosphere and oxalyl chloride (0.37 mL, 4.57 mmol) is added at room temperature, followed by 4-5 drops of DMF. The reaction mixture is heated to 50° C. for 1 h then cooled to room temperature and all volatiles are removed in vacuo to give a solid yellow residue, which is suspended in THF (30 mL). This suspension is added dropwise to a solution of N-methylpiperazine (0.51 mL, 4.57 mmol) and triethylamine (1.10 mL, 7.66 mmol) in H$_2$O (1 mL) at 0° C. The reaction is allowed to stir for 1 h at room temperature. Then all volatiles are removed in vacuo and the residual crude product is taken up in ethyl acetate, washed with H$_2$O and dried over MgSO$_4$. After filtration and removal of the solvents in vacuo the product is crystallized from ethyl acetate/hexanes to give a white powder. $^1$H-NMR (400 MHz, DMSO-$d_6$): 13.01 (s, 1H, NH), 8.61 (s, 1H), 8.11 (d, 2H), 7.54 (d, 2H), 7.21 (s, 1H), 3.71-3.45 (m, 4H), 2.39.2.21 (m, 4H), 2.19 (s, 3H). m. p.>320° C.

Example 1

Step 3: (4-Methylpiperazin-1-yl)-{4-[-(methyl-propyl-amino)-7H-pyrrolo[2,3-d]pyrimidin-6-yl]-phenyl}-methanone

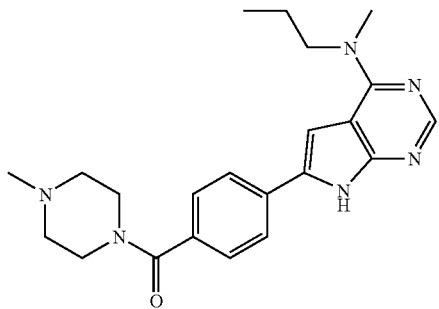

4-(4-Chloro-7H-pyrrolo[2,3-d]pyrimidin-6-yl)-(4-methyl-piperazin-1-yl)-methanone (99 mg, 0.28 mmol) is suspended in n-butanol (10 mL) and N-methyl-propyl amine is added at room temperature. The mixture is heated in a sealed tube to 80° C. for 16 h. The reaction mixture is then allowed to cool to room temperature again and the precipitated product is collected by filtration and washed with cold diethylether. It is dried in vauuo to give the title compound as a white powder. $C_{22}H_{28}N_6O$ : M+H=393.2; $^1$H-NMR (400 MHz, DMSO-$d_6$): 12.19 (s, 1H), 8.16 (s, 1H), 7.97 (d, 2H), 7.40 (d, 2H), 7.17 (s, 1H), 3.72 (t, 2H), 3.61-3.38 (m, 4H), 3.34 (s, 3H), 2.41-2.21 (m, 4H), 2.19 (s, 3H), 1.79-1.59 (m, 2H), 0.98 (t, 3H). m.p.=222-224° C.

Compounds of examples 2-23, wherein where Y of formula I is $(R_3)n$—X—, are synthesized in analogy to the above procedures (For compounds where X=—C(O)— only steps 1-3 for the starting material are performed for X=CH$_2$ all steps are permormed).

Structures, yields and analytical data are listed in table 1.

| Ex | $R_1$ | $R_2$ | $R_3$ | X | Analytical data |
|---|---|---|---|---|---|
| 2 | H | methyl | morpholinyl | O | $C_{24}H_{26}N_6O$: M+H=324.2; $^1$H-NMR(400MHz, DMSO-$d_6$): 11.98(s, 1H, NH), 8.10, (s, 1H), 7.71(d, 2H), 7.57(s, 1H), 7.33(d, 2H), 6.90(s, 1H), 3.61-3.51(m, 4H), 3.45(s, 3H), 2.36(m, 4H). m.p.=266-269° C. |
| 3 | methyl | methyl | N—Me-piperazinyl | O | $C_{20}H_{24}N_6O$: M+H=365.1; $^1$H-NMR(400MHz, MHz, DMSO-$d_6$): 12.19(s, 1H), 8.17(s, 1H), 7.97(d, 2H), 7.41(d, 2H), 7.19(s, 1H), 3.61-3.49(m, 4H), 3.38(s, 6H), 2.39-2.20(m, 4H), 2.18(s, 3H). m.p.=275-277° C. |
| 4 | methyl | methyl | N—Me-piperazinyl | H,H | $C_{20}H_{26}N_6$: M+H=350.5; $^1$H-NMR(400MHz, DMSO-$d_6$):12.01(s; 1H, NH), 8.17(s, 1H), 7.81(d, 2H), 7.34(d, 2H), 7.09(s, 1H), 3.42(s, 2H), 2.42-2.21(m, 8H), 2.17(s, 3H). m.p.=252-254° C. |
| 5 | methyl | methyl | N,N-diethylaminopropyl | O | $C_{22}H_{30}N_6O$: M+H=394.1; $^1$H-NMR(400MHz, DMSO-$d_6$): 12.20(s, 1H, NH), 8.59(s, 1H, NH), 8.17(s, 1H), 7.99(d, 2H), 7.82(d, 2H), 7.22(s, 1H), 3.39-3.21(m, 2H), 2.99(m, 4H), 2.61-2.51(m, 2H) 1.59-1.42(m, 2H), 0.99(t, 6H). |
| 6 | methyl | methyl | morpholinyl | O | $C_{19}H_{21}N_5O_2$: M+H=352.1; $^1$H-NMR(400MHz, DMSO-$d_6$): 12.10(s, 1H, NH), 8.27(s, 1H), 7.99(d, 2H), 7.48(d, 2H), 7.28(s, 1H), 3.71-3.62(m, 8H), 3.41(s, 6H). m.p.=316-318° C. $R_f$(EE/MeOH 8:2)=0.40. |
| 7 | methyl | methyl | N-(3-morpholinyl propyl)-amino | O | $C_{22}H_{28}N_6O_2$: M+H=409.1; $^1$H-NMR(400MHz, DMSO-$d_6$): 2.01(s, 1H, NH), 8.50(s, 1H, NH), 8.69(s, 1H), 8.02(d, 2H), 7.90(d, 2H), 7.29(s, 1H), 3.65-3.59(m, 4H), 3.47(s, 6H), 3.35-3.30(m, 2H), 2.49-2.32(m, 6H), 1.79-1.69(m, 2H). m.p.=260-262° C. $R_f$(EE/MeOH/NH$_3$ 9:1:0.2)=0.25. |
| 8 | N—Me-piperazinyl | N—Me-piperazinyl | | O | $C_{23}H_{29}N_7O$: M+H=421.1; $^1$H-NMR(400MHz, DMSO-$d_6$): 12.30(s, 1H, NH), 8.17(s, 1H), 7.98(d, 2H), 7.41(d, 2H), 7.21(s, 1H), 3.96-3.87(m, 4H), 3.61-3.54(m, 4H), 2.44-2.40(m, 4H), 2.39-2.22(m, 4H), 2.21(s, 3H), 2.18(s, 3H). m.p.=243-245° C. |
| 9 | N—Me-piperazinyl | N—Me-piperazinyl | | H,H | $C_{23}H_{31}N_7$: M+H=406.2; $^1$H-NMR(400MHz, DMSO-$d_6$): 12.16(s, 1H, NH), 8.13(s, 1H), 7.84(d, 2H), 7.31(d, 2H), 7.11(s, 1H), 3.90-3.87(m, 4H), 3.45(d, 2H), 2.51-2.46(m, 4H)2.44-2.41(m, 4H), 2.39-2.27(m, 4H), 2.22(s, 3H), 2.14(s, 3H). |
| 10 | methyl | ethyl | N—Me-piperazinyl | O | $C_{21}H_{28}N_6O$: M+H=379.1; $^1$H-NMR(400MHz, DMSO-$d_6$): 12.19(s, 1H, NH), 8.18(s, 1H), 7.95(d, 2H), 7.41(d, 2H), 7.17(s, 1H), 3.80(q, 2H), 3.61-3.54(m, 4H), |

-continued

| Ex | R₁ | R₂ | R₃ | X | Analytical data |
|----|----|----|----|----|-----------------|
| 11 | H | isopropyl | N—Me-piperazinyl | O | 2.39-2.21(m, 4H), 2.17(s, 3H), 1.19(t, 3H). $C_{21}H_{28}N_6O$: M+H=379.1; $^1$H-NMR(400MHz, DMSO-d$_6$): 12.09(s, 1H, NH), 8.16(s, 1H), 7.80(d, 2H), 7.42(d, 2H), 7.28(d, 1H, NH), 7.09(s, 1H), 4.41-4.34(m, 1H), 3.64-3.39(m, 4H), 2.39-2.21(m, 4H), 2.19(s, 3H), 1.21(d, 6H). |
| 12 | H | methyl | N—Me-piperazinyl | O | $C_{19}H_{22}N_6O$: M−H=349.1; $^1$H-NMR(400MHz, DMSO-d$_6$): 12.10(s, 1H, NH), 8.17(s, 1H), 7.80(d, 2H), 7.45(bs, 1H, NH), 7.40(d, 2H), 6.98(s, 1H), 3.64-3.39(m, 4H), 2.99(s, 3H), 2.40-2.21(m, 4H), 2.19(s, 3H). m.p=315° C. |
| 13 | H | isopropyl | N—Me-piperazinyl | H,H | $C_{21}H_{28}N_6$: M+H=365.2, $^1$H-NMR(400MHz, DMSO-d$_6$): 11.90(s, 1H, NH), 8.12, (s, 1H), 7.71(d, 2H), 7.38(d, 2H), 7.19(d, 1H, NH), 6.98, (s, 1H), 4.41-4.25(m, 1H), 3.42(s, 2H), 2.42-2.18(m, 8H), 2.16(s, 3H), 1.22(d, 6H). |
| 14 | Me | ethyl | N—Me-piperazinyl | H,H | $C_{21}H_{28}N_6$: M+H=365.2; $^1$H-NMR(400MHz, DMSO-d$_6$): 12.10(s, 1H, NH), 8.17(s, 1H), 7.82(d, 2H), 7.37(d, 2H), 7.01(s, 1H), 3.79(q, 2H), 3.43, (s, 2H), 2.41-2.18(m, 11H), 1.19(t, 3H). |
| 15 | H | 3-hydroxypropyl | N—Me-piperazinyl | O | $C_{21}H_{26}N_6O$: M−H=393.0; $^1$H-NMR(400MHz, DMSO-d$_6$): 12.10(s, 1H, NH), 8.17(s, 1H), 7.80(d, 2H), 7.51(s, 1H, NH), 7.41(d, 2H), 7.01(s, 1H), 4.59(t, 1H, OH), 3.60-3.49(m, 8H), 2.39-2.21(m, 4H), 2.19(s, 3H), 1.79(quint., 2H). m.p.=302-305° C. |
| 16 | H | methyl | N—Me-piperazinyl | H,H | $C_{19}H_{24}N_6$: M+H=337.1; $^1$H-NMR(400MHz, DMSO-d$_6$): 12.10(s, 1H, NH), 8.27(s, 1H), 7.85(d, 2H), 7.58(m, 1H, NH), 7.41(d, 2H), 7.00(s, 1H), 3.61(s, 2H), 3.12(d, 3H), 2.61-2.38(m, 8H), 2.29(s, 3H). |
| 17 | H | n-propyl | N—Me-piperazinyl | O | $C_{21}H_{26}N_6O$: M+H=379.2; $^1$H-NMR(400MHz, DMSO-d$_6$): 12.00(s, 1H, NH), 8.15(s, 1H), 7.80(d, 2H), 7.45(t, 1H, NH), 7.39(d, 2H), 7.00(s, 1H), 3.61-3.50(m, 4H), 3.40(dt, 2H), 2.39-2.20(m, 4H), 2.18(s, 3H), 1.60(qt, 2H), 0.95(t, 3H). m.p.=302-305° C. |
| 18 | H | n-propyl | N—Me-piperazinyl | H,H | $C_{21}H_{28}N_6$: M+H=365.2; $^1$H-NMR(400MHz, DMSO-d$_6$): 11.95(s, 1H, NH), 8.14(s, 1H), 7.70(d, 2H), 7.41(t, 1H, NH), 7.32(d, 2H), 6.92(d, 2H), 3.45(s, 2H), 3.44-3.38(m, 2H), 2.42-2.20(m, 8H), 2.15(s, 3H), 1.60(qt, 2H), 0.97(t, 3H). m.p.=232-234° C. |
| 19 | Me | n-propyl | N—Me-piperazinyl | H,H | $C_{22}H_{30}N_6$: M+H=379.2; $^1$H-NMR(400MHz, DMSO-d$_6$): 11.91(s, 1H, NH), 8.10(s, 1H), 7.79(d, 2H), 7.35(d, 2H), 6.99(s, 1H), 3.71(m, 2H), 3.41(s, 2H), 2.59-2.21(m, 8H), 2.19(t, 3H)1.65(m, 2H), 0.99(t, 3H). m.p.=220-221° C. |
| 20 | H | cyclo-propyl | N—Me-Piperazinyl | O | $C_{21}H_{24}N_6O$: M+H=377.1; $^1$H-NMR(400MHz, DMSO-d$_6$): 12.15(s, 1H), 8.17(s, 1H), 7.80(d, 2H), 7.61(s, 1H, NH), 7.40(d, 2H), 7.09(s, 1H), 3.61-3.39(m, 4H), 2.97(m, 1H), 2.39-2.21(m, 4H) 0.81-0.76(m, 2H), 0.60-0.53(m, 2H). |
| 21 | H | methyl | methylamino | O | $C_{15}H_{15}N_5O$: M+H=282.1; $^1$H-NMR(400MHz, DMSO-d$_6$): 12.10(s, 1H, NH), 8.40(s, 1H, NH), 8.17(s, 1H), 7.93(d, 2H), 7.69(d, 2H), 7.45(s, 1H, NH), 6.99(s, 1H), 2.99(s, 3H), 2.79(s, 3H). m.p.>300° C. R$_f$(ethyl acetate/MeOH 6:4)=0.64. |
| 22 | H | 2-(N,N-dimethyl amino)-ethyl | N—Me-piperazinyl | O | $C_{22}H_{29}N_7O$: M+H=408.2; $^1$H-NMR(400MHz, DMSO-d$_6$): 12.15(s, 1H, NH), 8.19(s, 1H), 7.81(d, 2H), 7.67(s, 1H, NH), 7.41(d, 2H), 7.08(s, 1H), 3.70-3.62(m, 2H), 3.39-3.32(m, 2H), 2.89-2.75(m, 4H), 2.51(s, 6H), 2.41-2.28(m, 4H), 2.17(s, 3H). m.p=268-270° C. |

-continued

| Ex | R₁ | R₂ | R₃ | X | Analytical data |
|---|---|---|---|---|---|
| 23 | H | 2-(N,N-dimethylamino)-ethyl | N—Me-piperazinyl | H,H | $C_{22}H_{29}N_7$: M+H=393.2; ¹H-NMR(400MHz, DMSO-$d_6$): 11.99(s, 1H), 8.12(s, 1H), 7.73(d, 2H), 7.39(s, 1H, NH), 7.80(d, 2H), 6.92(s, 1H), 4.19-4.12(m, 4H), 3.41(s, 2H), 3.17(s, 6H), 3.15(s, 3H), 2.42-2.31(m, 4H), 2.28-2.20(m, 4H). m.p.=decomp. |

Example 24

[6-(4-Imidazol-1-ylmethyl-phenyl)-7H-pyrrolo[2,3-d]pyrimidin-4-yl]-dimethylamine

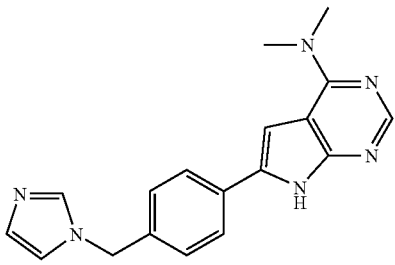

[6-(4-Chlormethyl-phenyl)-7H-pyrrolo[2,3]pyrimidin-4-yl]-dimethylamine (170 mg, 0.59 mmol) is dissolved in n-butanol (7 mL) at room temperature. Imidazole (326 mg, 4.80 mmol) and a catalytic amount of NaI are added and the mixture is heated to reflux for 1.5 h. It is allowed to cool to room temperature again, concentrated in vacuo to give a yellow solid which is purified by flash chromatography (SiO₂, ethyl acetate/MeOH 7:3) to give [6-(4-Imidazol-1-ylmethyl-phenyl)-7H-pyrrolo[2,3-d]pyrimidin-4-yl]-dimethylamine as a yellow solid. $C_{18}H_{18}N_6$: M+H=393.0; ¹H-NMR (400 MHz, DMSO-$d_6$): 12.11 (s, 1H, NH), 8.11 (s, 1H), 7.86 (d, 2H), 7.77 (s, 1H), 7.31 (d, 2H), 7.21 (s, 1H), 7.13 (s, 1H), 6.91 (s, 1H), 5.20 (s, 2H), 3.32 (s, 6H). m. p.=273-275° C.

Example 24

Step 1: 4-(4-Dimethylamino-7H-pyrrolo[2,3-d]pyrimidin-6-yl-benzoic acid ethylester

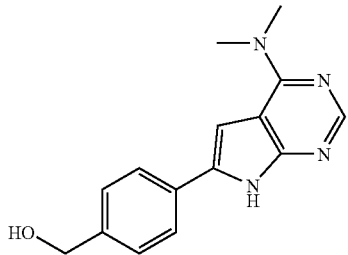

4-(4-Chloro-7H-pyrrolo[2,3]pyrimidin-6-yl)-benzoic acid ethyl ester (WO 97/02266; 900 mg, 3.00 mmol) is suspended in a 40% aqueous solution of dimethylamine (10 mL) and warmed to 60° C. in a sealed tube. The starting material dissolves gradually with simultaneous precipitation of product.

The reaction mixture is stirred for 1 h at 60° C. and then cooled to room temperature again. The product is isolated by filtration and washed with cold diethyl ether. After drying in vacuo the title compound is obtained as a yellow solid. $C_{17}H_{18}N_4O_2$: M+H=311.1; ¹H-NMR (400 MHz, DMSO-$d_6$): 12.31 (s, 1H, NH), 8.17 (s, 1H), 8.02 (d, 2H), 7.95 (d, 2H), 7.35 (s, 1H), 4.29 (q, 2H), 1.35 (t, 3H). m. p.=293-296° C.

Example 24

Step 2: [4-(4-Dimethylamino-7H-pyrrolo[2,3-d]pyrimidin-6-yl)-phenyl]-methanol

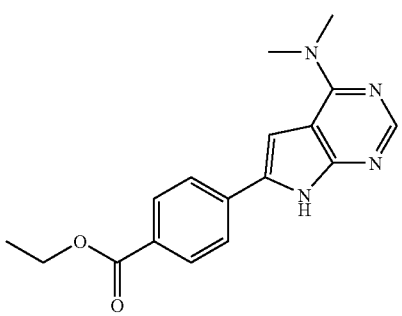

Li[AlH₄] (660 mg, 17.40 mmol) is suspended in THF (70 mL). The suspension is cooled in an ice bath and small portions of 4-(4-Dimethylamino-7H-pyrrolo[2,3-d]pyrimidin-6-yl-benzoic acid ethylester are added under an argon atmosphere. The reaction is stirred for 30 min. at room temperature and then heated to 50° C. for additional 30 min. It is then cooled to room temperature again and quenched by careful addition of dilute aqueous NaOH solution. The resulting suspension is stirred for 30 min. and then all inorganic salts are removed by filtration. The remainig solution is concentrated in vacuo to give a yellow solid which is titurated with hexanes. The product is isolated by filtration and dried in vacuo to give a white powder. $C_{15}H_{16}N_4O$: M+H=269.1; ¹H-NMR (400 MHz, DMSO-$d_6$): 13.01 (s, 1H, NH), 8.23 (s, 1H), 7.89 (d, 2H), 7.39 (d, 2H), 7.19 (s, 1H), 5.21 (s, 1H, OH), 4.55 (d, 2H), 3.35 (s, 6H). m. p.=306-309° C. $R_f$(ethyl acetate/MeOH 9:1)=0.30.

Example 24

Step 3: [6-(4-Chlormethl-phenyl)-7H-pyrrolo[2,3]pyrimidin-4-yl]-dimethyl-amine

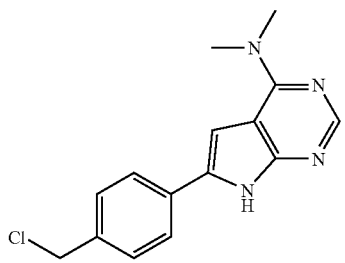

[4-(4-Dimethylamino-7H-pyrrolo[2,3-d]pyrimidin-6-yl)-phenyl]-methanol (510 mg, 1.90 mmol) is dissolved in toluene (15 mL) and cooled to −10° C. Thionyl chloride (2.70 mL, 38.0 mmol) is added dropwise and the reaction is stirred for 1 h at 0° C. and then for an additional hour at room temperature resulting in a yellow suspension. The precipitate is isolated by filtration. It is then partitioned between ethyl acetate and $H_2O$. The phases are separated and the aqueous phase is repeatedly extracted with ethyl acetate. Combined extracts are washed with brine and dried over $MgSO_4$, filtered and concentrated to give a yellow solid, which is dried in vacuo to give the title compound. $C_{15}H_{15}ClN_4$: M+H=287.1; $^1$H-NMR (400 MHz, DMSO-$d_6$): 12.11 (s, 1H), 8.12 (s, 1H), 7.89 (d, 2H), 7.42 (d, 2H), 7.18 (s, 1H), 4.79 (s, 2H), 3.38 (s, 6H). $R_f$(ethyl acetate/MeOH 9:1)=0.60.

Examples 25-29 ($R_1$ and $R_2$ are methyl), wherein Y of formula I is $(R_3)n$—X wherein X is $CH_2$ are prepared form [6-(4-chlormethyl-phenyl)-7H-pyrrolo[2,3]pyrimidin-4-yl]-dimethyl-amine according to the above procedure (Example 24). Analytical data is listed in table 2.

| Ex | $R_3$ | Analytical data |
|---|---|---|
| 25 | 2-pyrrolyl | $C_{19}H_{19}N_5$: M+H=318.1; $^1$H-NMR(400MHz, DMSO-$d_6$): 12.01(s, 1H, NH), 10.15(s, 1H, NH), 8.15(s, 1H), 7.82(d, 2H), 7.29(d, 2H), 7.11(s, 1H), 6.61(m, 1H), 5.97(m, 1H), 5.80(m, 1H), 3.39(s, 6H). m.p. 285-287° C., $R_f$(ethyl acetate/MeOH 9:1)=0.63 |
| 26 | n-butoxy | $C_{19}H_{24}N_4O$: M+H=325.1; $^1$H-NMR(400MHz, DMSO-$d_6$): 12.10(s, 1H, NH), 8.21(s, 1H), 7.89(d, 2H), 7.39(d, 2H), 7.25(s, 1H), 4.49(s, 2H), 3.49(t, 2H), 3.41(s, 6H), 1.61-1.51(m, 2H), 1.43-1.35(m, 2H), 0.90(t, 3H). m.p. 186-188° C., $R_f$(ethyl acetate/MeOH 9:1)=0.66. |
| 27 | 1-tetrazolyl | $C_{16}H_{16}N_8$: M+H=320.2; $^1$H-NMR(400MHz, DMSO-$d_6$): 13.40(s, 1H, NH), 9.55(s, 1H), 8.27(s, 1H), 8.00(d, 2H), 7.49(d, 2H), 7.41(s, 1H), 5.76(s, 2H), 2.51(s, 6H). m.p.=275-278° C. |
| 28 | 4-(hydroxypropyl)-amino | $C_{18}H_{23}N_5O$: M+H=326.2; $^1$H-NMR(400MHz, DMSO-$d_6$): 12.06(s, 1H, NH), 8.11(s, 1H), 7.18(d, 2H), 7.34(d, 2H), 7.09(s, 1H), 4.45(brs, 1H, OH), 3.68(s, 2H), 3.46(t, 2H), 3.34(s, 6H), 2.55(t, 2H), 1.58(quint, 2H). m.p.=218-220° C., $R_f$(ethyl acetate/MeOH/$NH_3$ 6:4:0.2)=0.31. |
| 29 | N,N-(2-methoxyethyl)methyl-amino | $C_{19}H_{25}N_5O$: M+H=340.2; $^1$H-NMR(400MHz, DMSO-$d_6$): 12.07(s, 1H, NH), 8.11(s, 1H), 7.82(d, 2H), 7.33(d, 2H), 7.10(s, 1H), 3.50(s, 2H), 3.45(t, 2H), 3.34(s, 6H), 3.23(s, 3H), 2.52(m, 2H), 2.17(s, 3H). m.p.=157-158° C., $R_f$(ethyl acetate/MeOH 6:4)=0.37. |

Example 30

2-[4-(4-(3-Morpholin-4-yl-propylamino)-7H-pyrrolo][2,3-d]pyrimidin-6-yl]-phenyl]-pentan-3-ol

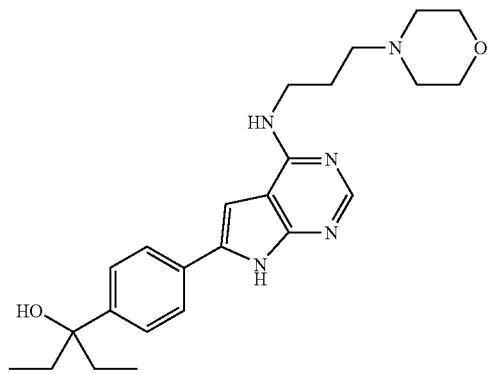

4-[4-(3-Morpholin-4-yl-propylamino)-7H-pyrrolo[2,3-d]pyrimidin-6-yl]benzoic acid ethyl ester (147 mg, 0.36 mmol) is suspended in THF and cooled to −70° C. under an argon atmosphere. Ethylmagnesium bromide (2.2 mL, 1 M sol. In THF) is added dropwise via a cannula. The reaction mixture is stirred for 30 min. at −70° C. and then allowed to warm to room temperature. It is stirred for an additional 1 h and then worked up by addition of ethyl acetate, dilute aqueous HCl and $H_2O$. The phases are separated and the aqueous layer is repeatedly extracted with ethyl acetate. Combined organic extracts are washed with brine and dried over $MgSO_4$. After filtration all volatiles are removed in vacuo to give 2-[4-(4-(3-Morpholin-4-yl-propylamino)-7H-pyrrolo][2,3-d]pyrimidin-6-yl]-phenyl]-pentan-3-ol as a white powder. $C_{24}H_{33}N_5O_2$: M+H=424.3; $^1$H-NMR (400 MHz, DMSO-$d_6$): 11.95 (s, 1H, NH), 8.15 (s, 1H), 8.15 (s, 1H), 7.71 (d, 2H), 7.42-7.39 (m, 3H), 6.83 (s, 1H), 4.58 (s, 1H, OH), 3.59 (q, 4H), 3.51-3.43 (m, 2H), 2.39-2.23 (m, 6H), 1.81-1.62 (m, 6H), 0.62 (t, 6H). m. p.=175-177° C.

Example 30

Step 1: 4-[4-(3-Morpholin-4-yl-propylamino)-7H-pyrrolo[2,3-d]pyrimidin-6-yl]benzoic acid ethylester

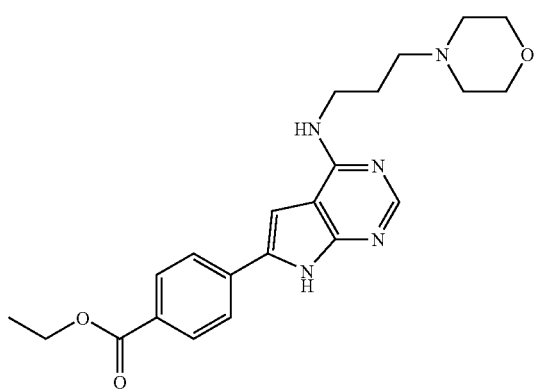

4-(4-Chloro-7H-pyrrolo[2,3]pyrimidin-6-yl)-benzoic acid ethyl ester (WO 97/02266, 271 mg, 6.64 mmol) is suspended in n-butanol (30 mL). 3-Aminoppropyl-morpholine (519 mg, 3.6 mmol) is added. The reaction mixture is heated to 80° C. for 72 h and then allowed to cooled to 0° C. and the yellow precipitate is isolated by filtration, washed with cold diethyl ether and dried in vacuo to give the title compound as a yellow powder. $C_{22}H_{27}N_5O_3$: M+H=410.2; $^1$H-NMR (400 MHz, DMSO-$d_6$): 12.20 (s, 1H, NH), 8.17 (s, 1H), 8.00 (d, 2H), 7.91 (d, 2H), 7.60 (t, 1H, NH), 7.16 (s, 1H), 4.31 (q, 2H), 3.59-3.53 (m, 4H), 3.51-3.42 (m, 2H), 2.41-2.25 (m, 6H), 1.81-1.70 (m, 2H), 1.37 (t, 3H). m. p.=231-234° C.

Example 30

Step 2: 2-[4-(4-(3-Morpholin-4-yl-propylamino)-7H-pyrrolo][2,3-d]pyrimidin-6-yl]-phenyl]-pentan-3-ol Examples 31-35, wherein where Y is of formula

are prepared form 4-(4-chloro-7H-pyrrolo[2,3]pyrimidin-6-yl)-benzoic acid ethyl ester according to the above procedure. Analytical data is listed in table 3.

| Ex | R1 | R2 | R3 | Analytical data |
|---|---|---|---|---|
| 31 | 2-methoxyethyl | 2-methoxyethyl | methyl | $C_{21}H_{28}N_4O_3$: M+H=385.2; $^1$H-NMR(400MHz, DMSO-$d_6$): 12.09(s, 1H, NH), 7.99(s, 1H), 7.79(d, 2H), 7.42(d, 2H), 6.80(s, 1H), 5.01(s, 1H, OH), 3.98-3.92(m, 4H), 3.41-3.38(m, 4H), 3.24(s, 6H), 1.41(s, 6H). m.p.=165-167° C. |
| 32 | 2-methoxyethyl | 2-methoxyethyl | ethyl | $C_{23}H_{32}N_4O_3$: M+H=413.3 $^1$H-NMR(400MHz, DMSO-$d_6$): 12.01(s, 1H), 8.12(s, 1H), 7.79(d, 2H), 7.40(d, 2H), 6.80(s, 1H), 4.58(s, 1H, OH), 3.98-3.89(m, 4H), 3.61-3.54(m, 4H), 3.24(s, 6H), 1.80-1.61(m, 4H), 0.62(t, 6H). m.p.=83-85° C. |
| 33 | H | 3-(1-pyrrolidinyl)-propylamino | ethyl | $C_{24}H_{29}N_5O$: M+H=404.3 $^1$H-NMR(400MHz, DMSO-$d_6$): 11.99(s, 1H, NH), 8.13(s, 1H), 7.70(d, 2H), 7.41(t, 1H, NH), 7.39(d, 2H), 6.89(s, 1H), 6.79(s, 2H), 5.99(s, 2H), 4.58(s, 1H, OH), 3.99(t, 2H), 3.42-3.38(m, 2H), 2.04(dt, 2H), 1.80-1.60(m, 4H), 0.85(t, 6H). m.p.=180-182° C. |
| 34 | methyl | methyl | methyl | $C_{17}H_{20}N_4O$: M+H=297.1 $^1$H-NMR(400MHz, DMSO-$d_6$): 12.02(s, 1H, NH), 8.11(s, 1H), 7.79(d, 2H), 7.43(d, 2H), 7.07(s, 1H), 5.01(s, 1H, OH), 3.32(s, 6H), 1.41(s, 6H). m.p.>300° C. |
| 35 | H | methyl | methyl | $C_{16}H_{18}N_4O$: M+H=283.1 $^1$H-NMR(400MHz, DMSO-$d_6$): 11.99(s, 1H, NH), 8.17(s, 1H), 7.69(d, 2H), 7.40(m, 1H, NH), 7.28(d, 2H), 6.81(s, 1H), 2.99(d, 3H), 2.91-2.82(m, 1H, OH); 1.21(d, 6H). m.p.=280-283° C. |

Example 36

Dry-filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation process: The mentioned substances are pulverised and forced through a sieve of 0.6 mm mesh size. 0.33 g portions of the mixture are introduced into gelatin capsules using a capsule-filling machine.

Example 37

Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 litre |
| Tween 80 | 1 litre |

Preparation process: The active ingredient is pulverised and suspended in PEG 400 (polyethylene glycol having an $M_r$ of from approx. 380 to approx. 420, Fluka, Switzerland) and Tween® 80 (polyoxyethylene sorbitan monolaurate, Atlas Chem. Ind. Inc., USA, supplied by Fluka, mSwitzerland) and ground in a wet pulveriser to a particle size of approx. from 1 to 3 μm 0.43 g portions of the mixture are then introduced into soft gelatin capsules using a capsule-filling machine.

Example 38

Inhibition of the tyrosine kinase activity of BcrAbl, c-Abl, c-Raf-1, EGF-R (HER-1 (HER-2) and VEGF receptor (KDR).

| Example No. | bcrabl32DcEL/ Average<32Dp210IC50 [umol l−1]> | c-Abl IC50 [umol l−1] | c-Raf-1/ %-inh. @10 M [%] | HER-1/ %-inh. @10 M [%] | HER-2/%- inh. @10 M [%] | KDR (% inh) |
|---|---|---|---|---|---|---|
| 2 | 0.2919 | 0.03495 | 56 | 78 | 65 | 77 |
| 3 | 0.7974 | 0.019 | 51 | 59 | 78 | 85 |
| 4 | 0.72855 | 0.032 | 40 | 64 | 87 | 86 |
| 5 |  | 0.021 | 48 | 58 | 78 | 79 |
| 6 | 0.9351 | 0.0026 | 63 | 70 | 80 | 83 |
| 7 | 0.9168 | 0.025 |  | 59 | 71 | 79 |
| 12 |  | 0.004 | 22 | 85 | 85 | 67 |
| 15 |  | 0.014 | 64 | 94 | 88 | 80 |
| 16 | 0.0508 | 0.011 | 67 | 94 | 93 | 85 |
| 17 | 1.6286 | 0.005 | 100 | 95 | 87 | 81 |
| 18 | 0.9394 | 0.006 | 100 | 98 | 94 | 83 |
| 19 | 2.0682 | 0.011 | 100 | 97 | 89 | 85 |
| 24 | 0.7904 | 0.011 | 100 | 93 | 93 | 75 |
| 25 | 10 | 0.009 | 96 | 57 | 39 | 50 |
| 27 | 0.903 | 0.01 | 100 | 83 | 75 | 58 |
| 28 | 0.40855 |  | 80 | 85 | 85 | 76 |
| 29 | 0.2736 |  | 77 | 79 | 79 | 76 |
| 33 | 2.4325 | 0.13 | 48 | 98 | 88 | 84 |
| 34 | 0.9438 | 0.021 | 50 | 54 | 57 | 66 |
| 35 |  | 0.01 | 44 | 90 |  | 76 |

The invention claimed is:
1. A compound of formula I,

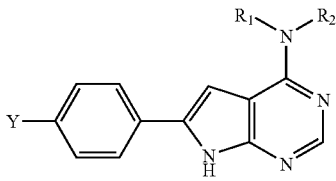

wherein
R$_1$, and R$_2$ are independently hydrogen, lower alkyl, cycloalkyl, hydroxy-lower alkyl, lower alkoxy-lower alkyl, lower alkyl-amino-lower alkyl, heterocycle-lower alkyl;
or R$_1$ and R$_2$ can join together to form a N-heterocycle or lower alkyl-N-heterocycle all of which may be unsubstituted or substituted;
Y is (R$_3$)$_n$—X— or A(R$_3$)(R$_3$)C—
wherein
X is lower alkylene or carbonyl;
A is hydroxy;
R$_3$ is lower alkyl, lower alkoxy, amino, hydroxy, heterocyclic, heteroaryl, lower alkyl-heterocycle, heterocycle-lower alkyl, lower alkyl-amino-lower alkyl, heterocycle-lower alkyl-amino, lower alkyl-amino, hydroxy-lower alkyl-amino, amino substituted by lower alkoxy-lower alkyl and lower alkyl;
n is 1 or 2;
wherein heterocyclic is selected from pyrrolidinyl, tetrahydrothiophenyl, tetrahydrofuranyl, piperidinyl, pranyl, pyrazolidinyl, oxiranyl, dioxanyl, imidazolinyl, imidazolidinyl, morpholinoyl and piperazinyl;
cycloalkyl is selected from cyclopropyl, cyclobutyl, cyolopentyl, cyclohexyl, cycloheptyl and cyclooctyl;
N-heterocyclic is selected from pyrrolidinyl, imidazolinyl, imidazolidinyl, piperidinyl, morpholinoyl, and piperazinyl;
heteroaryl is selected from pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl and thienyl;
or a pharmaceutically acceptable salt thereof.

2. A compound of formula I according to claim 1
R$_1$ and R$_2$ are independently hydrogen, methyl, ethyl, propyl, cyclopropyl, hydroxy-propyl, dimethylamino-ethyl, morpholinyl-propyl, methoxy-ethyl, pyrrolidinyl-propyl;
or R$_1$ and R$_2$ can join together to form a piperazinyl or methyl-piperazinyl,
Y is (R$_3$)$_n$—X—or A(R$_3$)(R$_3$)C—;
wherein
X is CH$_2$ or —C(O)—;
A is hydroxy;
n is 1;
R$_3$ is methylene, ethylene, butoxy, morphelinyl, piperazinyl, pyrrolyl, tetrazoyl, imidazoyl, methyl-piperazinyl, diethyl-amino-propyl, morpholino-propyl-amino, methyl-amino, hydroxy-propyl-amino, (methoxy-ethyl) methyl-amino;
or a pharmaceutically acceptable salt thereof.

3. A compound selected from the group consisting of methyl-{6-[4-(4-methyl-piperazin-1-ylmethyl)phenyl]-7H-pyrrolo[2,3-d]pyrimidin-4-yl}-propylamine;
[4-(4-methylamino-7H-pyrrolo[2,3-d]pyrimidin-6-yl)-phenyl]-morpholin-4-yl-methanone;
[4-(4-dimethylamino-7H-pyrrolo[2,3-d]pyrimidin-6-yl)-phenyl]-(4-methyl-piperazin-1-yl)-methanone;
dimethyl-{6-[4-(4-methyl-piperazin-1-ylmethyl)-phenyl]-7H-pyrrolo[2,3-d]pyrimidin-4-yl}-amine;
N-(3-diethylamino-propyl)-4-(4-dimethylamino-7H-pyrrolo[2,3-d]pyrimidin-6-yl)-benzamide;
[4-(4-dimethylamino-7H-pyrrolo[2,3-d]pyrimidin-6-yl)-phenyl]-morpholin-4-yl-methanone;
4-(4-dimethylamino-7H-pyrrolo[2,3-d]pyrimidin-6-yl)-N-(3-morpholin-4-yl-propyl)-benzamide;
(4-methyl-piperazin-1-yl)-{4-[4-(4-methyl-piperazin-1-yl)-7H-pyrrolo[2,3-d]pyrimidin-6-yl]-phenyl}-methanone;
4-(4-methyl-piperazin-1-yl)-6-[4-(4-methyl-piperazin-1-ylmethyl)-phenyl]-7H-pyrrolo[2,3-d]pyrimidine;
{4-[4-(ethyl-methyl-amino)-7H-pyrrolo[2,3-d]pyrimidin-6-yl]-phenyl}-(4-methyl-piperazin-1-yl)-methanone;
[4-(4-isopropylamino-7H-pyrrolo[2,3-d]pyrimidin-6-yl)-phenyl]-(4-methyl-piperazin-1-yl)-methanone;
[4-(4-methylamino-7H-pyrrolo[2,3-d]pyrimidin-6-yl)-phenyl]-(4-methyl-piperazin-1-yl)-methanone;
isopropyl-{6-[4-(4-methyl-piperazin-1-ylmethyl)-phenyl]-7H-pyrrolo[2,3-d]pyrimidin-4-yl}-amine;
ethyl-methyl-{6-[4-(4-methyl-piperazin-1-ylmethyl)-phenyl]-7H-pyrrolo[2,3-d]pyrimidin-4-yl}-amine;
{4-(4-(3-hydroxy-propylamino)-7H-pyrrolo(2,3-d]pyrimidin-6-yl]-phenyl}-(4-methyl-piperazin-1-yl)-methanone;
methyl-{6-[4-(4-methyl-piperazin-1-ylmethyl)-phenyl]-7H-pyrrolo[2,3-d]pyrimidin-4-yl}-amine;
(4-Methyl-piperazin-1-yl)-[4-(4-propylamino-7H-pyrrolo[2, 3-d]pyrimidin-6-yl)-phenyll-methanone;
{6-[4-(4-Methyl-piperazin-1-ylmethyl)-phenyl]-7H-pyrrolo[2,3-d]pyrimidin-4-yl}-propyl-amine;
[4-(4-Cyclopropylamino-7H-pyrrolo[2,3-d]pyrimihidin-6-yl)-phenyl]-(4-methyl-piperazin-1-yl)-methanone;
N-methyl-4-(4-methylamino-7H-pyrrolo[2,3-d]pyrimidin-6-yl)-benzamide;
{4-(4-(2-Dimethylamino-ethylamino)-7H-pyrrolo2,3-d]pyrimidin-6-yl]-phenyl}-(4-methyl-piperazin-1-yl)-methanone;
N,N-dimethyl-N'-{6-[4-(4-methyl-piperazin-1-ylmethyl)-phenyl]-7H-pyrrolo[2,3-d]pyrimidin-4-yl)-ethane-1,2-diamine;
[6-(4-Imidazol-1-ylmethyl-phenyl)-7H-pyrrolo[2,3-d]pyrimidin-4-yl]-dimethyl-amine;
dimethyl-{6-[4-(1H-pyrrol-2-ylmethyl)-phenyl]-7H-pyrrolo[2,3-d]pyrimidin-4-yl}-amine;
[6-(4-Butoxymethyl-phenyl)-7H-pyrrolo[2,3-d]pyrimidin-4-yl]-dimethyl-amine;
dimethyl-[6-(4-tetrazol-1-ylmethyl-phenyl)-7H-pyrrolo[2,3-d]pyrimidin-4yl]-amine;
3-[4-(4-Dimethylamino-7H-pyrrolo[2,3-d]pyrimidin-6-yl)-benzylamino]-propan-1-ol;
(6-(4-{[(2-Methoxy-ethyl)-methyl-amino]-methyl}-phenyl)-7H-pyrrolo[2,3-d]pyrimidin-4-yl]-dimethyl-amine;
3-{4-[4-(3-Morpholin-4-yl-propylamino)-7H-pyrrolo[2, 3-d]pyrimidin-6-yl]-phenyl}-pentan-3-ol;
2-(4-{4-[Bis-(2-methoxy-ethyl)-amino]-7H-pyrrolo[2,3-d]pyrimidin-6-yl}-phenyl)-propan-2-ol;

3-(4-{4-[Bis-(2-methoxy-ethyl)-amino]-7H-pyrrolo[2,3-d]pyrimidin-6-yl}-phenyl)-pentan-3-ol;

3-{4-[4-(3-Pyrrol-1-yl-propylamino)-7H-pyrrolo(2,3-d]pyrimidin-6-yl]-phenyl)-pentan-3-ol;

2-[4-(4-Dimethylamino-7H-pyrrolo[2,3-d]pyrimidin-6-yl)-phenyl]-propan-2-ol;

2-[4-(4-Methylamino-7H-pyrrolo[2,3-d]pyrimidin-6-yl)-phenyl]-propan-2-ol;

or a pharmaceutically acceptable salt thereof.

4. A compound of formula I according to claim 1 selected from the group consisting of

[4-(4-methylamino-7H-pyrrolo[2,3-d]pyrimidin-6-yl)-phenyl]-morpholin-4-yl-methanone;

[4-(4-dimethylamino-7H-pyrrolo[2,3-d]pyrimidin-6-yl)-phenyl]-morpholin-4-yl-methanone;

{4-[4-(ethyl-methyl-amino)-7H-pyrrolo[2,3-d]pyrimidin-6-yl]-phenyl)-(4-methyl-piperazin-1-yl)-methanone;

isopropyl-{6-(4-(4-methyl-piperazin-1-ylmethyl)-phenyl]-7H-pyrrolo[2,3-d]pyrimidin-4-yl}-amine;

ethyl-methyl-{6-[4-(4-methyl-piperazin-1-ylmethyl)-phenyl]-7H-pyrrolo[2,3-d]pyrimidin-4-yl}-amine;

methyl-{6-[4-(4-methyl-piperazin-1-ylmethyl)-phenyl]-7H-pyrrolo[2,3-d]pyrimidin4-yl}-amine;

[6-(4Imidazol-1-ylmethyl-phenyl)-7H-pyrrolo[2,3-d]pyrimidin-4-yl]-dimethyl-amine;

2-[4-(4-Dimethylamino-7H-pyrrolo[2,3-d]pyrimidin-6-yl)-phenyl]-propan-2-ol;

or a pharmaceutically acceptable salt thereof.

5. A pharmaceutical composition comprising a compound of formula I or a pharmaceutically acceptable salt thereof according to claim 1 together with at least one pharmaceutically acceptable carrier.

* * * * *